(12) United States Patent
Brown et al.

(10) Patent No.: US 9,371,729 B2
(45) Date of Patent: Jun. 21, 2016

(54) PERMEAMETER PROBE

(71) Applicant: J.R. Simplot Company, Boise, ID (US)

(72) Inventors: Brock Brown, Afton, WY (US); Ron Hager, Thayne, WY (US); Grant J. Williams, Afton, WY (US)

(73) Assignee: J.R. Simplot Company, Boise, ID (US)

( * ) Notice: Subject to any disclaimer, the term of this patent is extended or adjusted under 35 U.S.C. 154(b) by 375 days.

(21) Appl. No.: 13/922,172

(22) Filed: Jun. 19, 2013

(65) Prior Publication Data

US 2013/0340517 A1 Dec. 26, 2013

Related U.S. Application Data

(60) Provisional application No. 61/662,224, filed on Jun. 20, 2012.

(51) Int. Cl.
*E21B 49/00* (2006.01)
*G01N 33/24* (2006.01)

(52) U.S. Cl.
CPC ............. *E21B 49/00* (2013.01); *G01N 33/24* (2013.01)

(58) Field of Classification Search
CPC ................................ E21B 49/00; G01N 33/24
See application file for complete search history.

(56) References Cited

U.S. PATENT DOCUMENTS

| | | | | |
|---|---|---|---|---|
| 3,257,170 A * | 6/1966 | Marcus | ............... | B01D 17/0214 210/424 |
| 4,164,139 A | 8/1979 | Jones | | |
| 4,331,189 A * | 5/1982 | Joyner | ............... | A47J 43/284 141/331 |
| 4,934,420 A * | 6/1990 | Radna | ............... | B01D 17/0214 141/331 |
| 4,969,111 A * | 11/1990 | Merva | ............... | E21B 49/008 324/694 |
| 5,548,991 A * | 8/1996 | Ritson | ............... | G01N 33/24 175/21 |
| 6,308,563 B1 * | 10/2001 | Hubbell | ............... | E21B 47/042 73/152.51 |
| 6,810,755 B1 * | 11/2004 | Pask | ............... | G01N 15/0826 73/152.41 |
| 6,938,461 B1 | 9/2005 | Johnson | | |
| 6,976,386 B1 * | 12/2005 | Grover | ............... | E21B 49/08 137/78.2 |
| 7,059,174 B2 * | 6/2006 | Ranjan | ............... | E21B 49/008 73/38 |
| 7,677,419 B2 | 3/2010 | DiGregorio | | |
| 2005/0236063 A1 | 10/2005 | Digregorio et al. | | |
| 2011/0203368 A1 * | 8/2011 | Zhang | ............... | G01F 19/00 73/426 |

FOREIGN PATENT DOCUMENTS

| | | |
|---|---|---|
| CN | 190681 | 1/2007 |
| CN | 101382480 | 3/2009 |
| SU | 1682891 | 10/1991 |

OTHER PUBLICATIONS

International Searching Authority; International Search Report and Written Opinion for PCT/US2013/046660 dtd Nov. 27, 2013.
"Standard Test Method for Field Measurement of Hydraulic Conductivity Using Borehole Infiltration" ASTM Committee p. 1-16 dated Jan. 31, 2012.

(Continued)

*Primary Examiner* — John Fitzgerald
(74) *Attorney, Agent, or Firm* — Parsons Behle & Latimer

(57) ABSTRACT

A permeameter probe, configured for performing hydraulic conductivity measurements of soil, includes a standpipe having a top section, a transitional section, and a bottom section. The transitional section provides a gradual change in diameter between the larger diameter bottom section and the smaller diameter top section. The standpipe also includes a lower lip for forming a pressure fitting between the standpipe and a casing placed in a borehole.

15 Claims, 6 Drawing Sheets

(56) References Cited

OTHER PUBLICATIONS

"Introduction of Material Engineering" p. 121-130, Chemical Industry Press; Bi Dasen, et al., Chemical Industry Press dated Jun. 30, 2010.

State Intellectual Property Office of the People's Republic of China; First Office Action for Application No. 201380040247A dated Jan. 22, 2016.

Australian Government IP Australia; Examination Report Report No. 1 for Application No. 2013313312 dated Feb. 19, 2016.

* cited by examiner

PERMEAMETER PROBE

PRIORITY CLAIM

The present application claims the benefit of U.S. Provisional Patent Application Ser. No. 61/662,224, filed on Jun. 20, 2012 and entitled PERMEAMETER PROBE, the disclosure of which is incorporated herein by reference in its entirety.

BACKGROUND

The present disclosure relates to a device for measuring the hydraulic conductivity of porous materials in situ, and more particularly relates to a permeameter probe for use with borehole infiltration, the probe measuring the hydraulic conductivity of soil.

When preparing to use land for agricultural, mining, or other developmental purposes, it is often necessary to obtain measurements of the hydraulic conductivity of soil. Hydraulic conductivity values provide a basis for safe and economical land use. These measurements are important considerations in design and construction of building and roadway structures and are central to planning for waste water applications, irrigation systems, mining operations, and many other systems. Further, the measurements may be necessary in and of themselves to comply with local ordinances and/or federal regulations.

Approximation of soil hydraulic conductivity at a particular location using available methods is both challenging and expensive, often requiring multiple measurements over a period of several days in order to obtain reliable results. For many applications, the soil hydraulic conductivity must be measured in situ, rather than by measurement of a sample. This is because the very removal of the sample from the targeted location changes the conditions of the sample.

One system and method for measuring soil hydraulic conductivity prescribed by the prior art uses borehole infiltration with a permeameter probe. Publication ASTM D6391-11, the entirety of which is incorporated herein by reference, sets forth exemplary standards for borehole testing. FIG. 1 is a depiction of a prior art permeameter probe 100, wherein a casing 120 is placed at the bottom of borehole 110. An annular sealant 125 is placed around the bottom of the casing 120 along the bottom of the borehole 110 to ensure a predictable measurement. A secondary sealant 126 is also placed around the periphery of the casing 120, between the casing 120 and the walls of the borehole 110, to support the shape of the casing 120 and the integrity of the borehole 110. A cap 130 is located on the top of the casing 120. The cap 130 includes a vertically protruding nozzle 140 that attaches to a standpipe 150. A first coupling 135 attaches the cap 130 to the casing 120 and a second coupling 145 attaches the nozzle 140 to the standpipe 150. In this example, where the prior art permeameter probe 100 comprises a constant-head arrangement, the standpipe 150 further includes a top cap 160, enclosing the top of the standpipe 150, with a third coupling 155 attaching the top cap 160 to the top of the standpipe 150. The permeameter probe 100 further comprises a rubber stopper 170 for enclosing the standpipe 150, and a compression fitting 175, through which is inserted a mariotte tube 180. A scale 190 is also provided to measure the amount of water that has been absorbed by the soil over a period of time.

Because in situ measurements are often demanded, due to the relative simplicity and general acceptance in the field, the constant-head permeameter probe 100 described above remains a commonly used solution. This and other prior art devices, however, suffer from various issues, such as frequent leakage from the various couplings and lengthy setup times.

SUMMARY

The present disclosure provides a permeameter probe that allows for convenient construction, consistent results, fewer errors, and which provides a probe which will perform the test for hydraulic conductivity of soil according to widely accepted methods. In particular, the present disclosure provides an apparatus for measuring the hydraulic conductivity of soil in connection with a borehole formed in the soil at a location to be tested. The apparatus generally includes a casing placed in the borehole and an annular sealant placed around the bottom of the casing. The apparatus further includes a standpipe according the present disclosure, which is formed as a single, unitary piece that is substantially transparent. The standpipe is formed having a base section with a first diameter, a top section with a second, smaller diameter, and a transitional section connecting the base section and the top section. The base section includes a lower lip which forms a pressure fitting with the casing. The diameter of the transitional section changes gradually along the vertical axis of the standpipe. For constant-head measurements, the apparatus also includes a stopper and a mariotte tube, wherein the stopper is placed in the top end of the top section and the mariotte tube enters the standpipe through a hole in the stopper.

Other systems, methods, features, and advantages of the present disclosure will be or become apparent to one with skill in the art upon examination of the following drawings and detailed description. The features, functions and advantages that have been discussed can be achieved independently in various embodiments of the present invention or may be combined in yet other embodiments further details of which can be seen with reference to the following description and drawings.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION

In the following description, reference is made to the accompanying drawings, which form a part hereof, and in which is shown, by way of illustration, various embodiments of the present disclosure. It is understood that other embodiments may be utilized and changes may be made without departing from the scope of the present invention.

Figure 1:
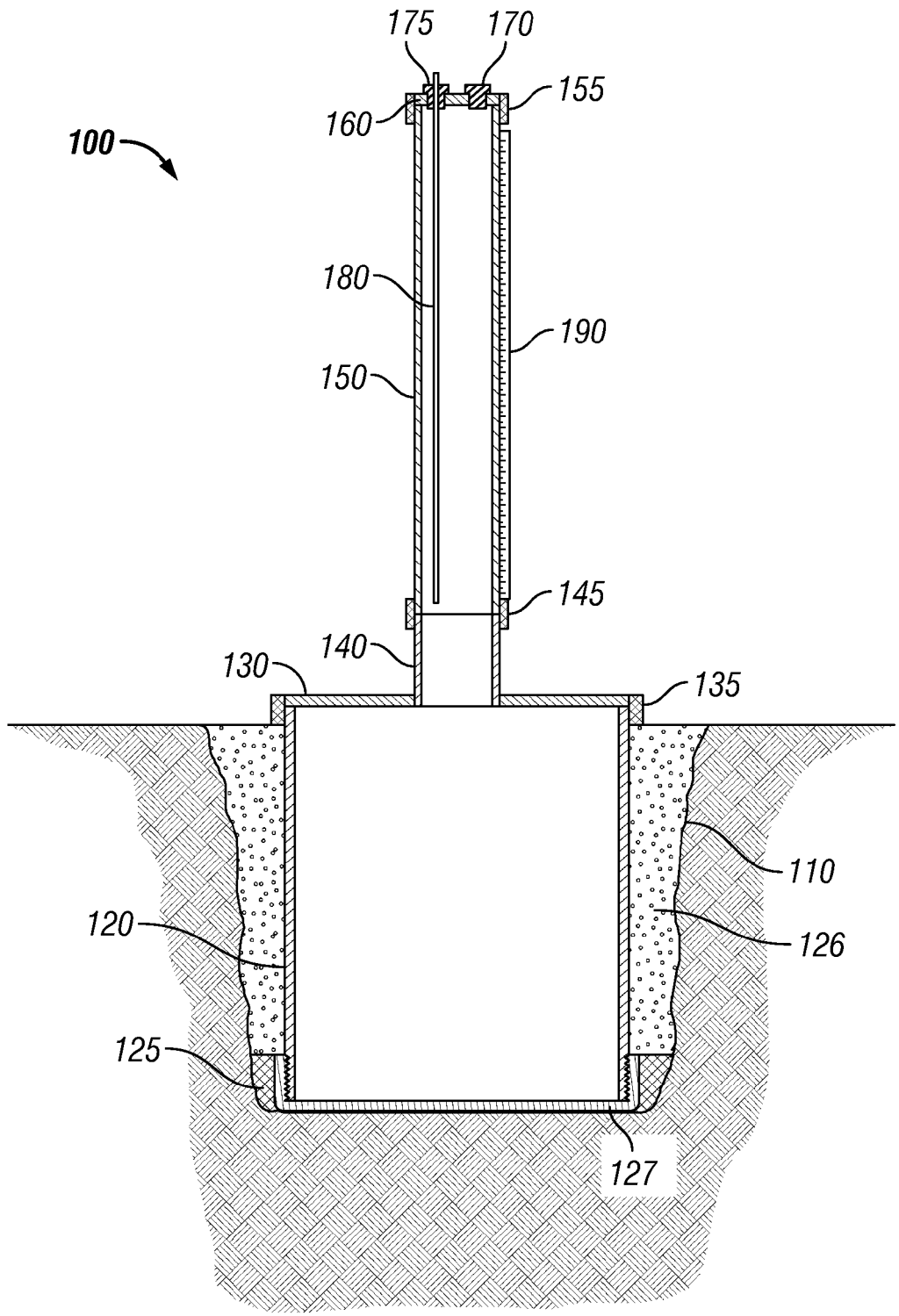
FIG. 1 is a sectional view of one example of a permeameter probe for in situ measurements of hydraulic conductivity according to the prior art.
Figure 2:
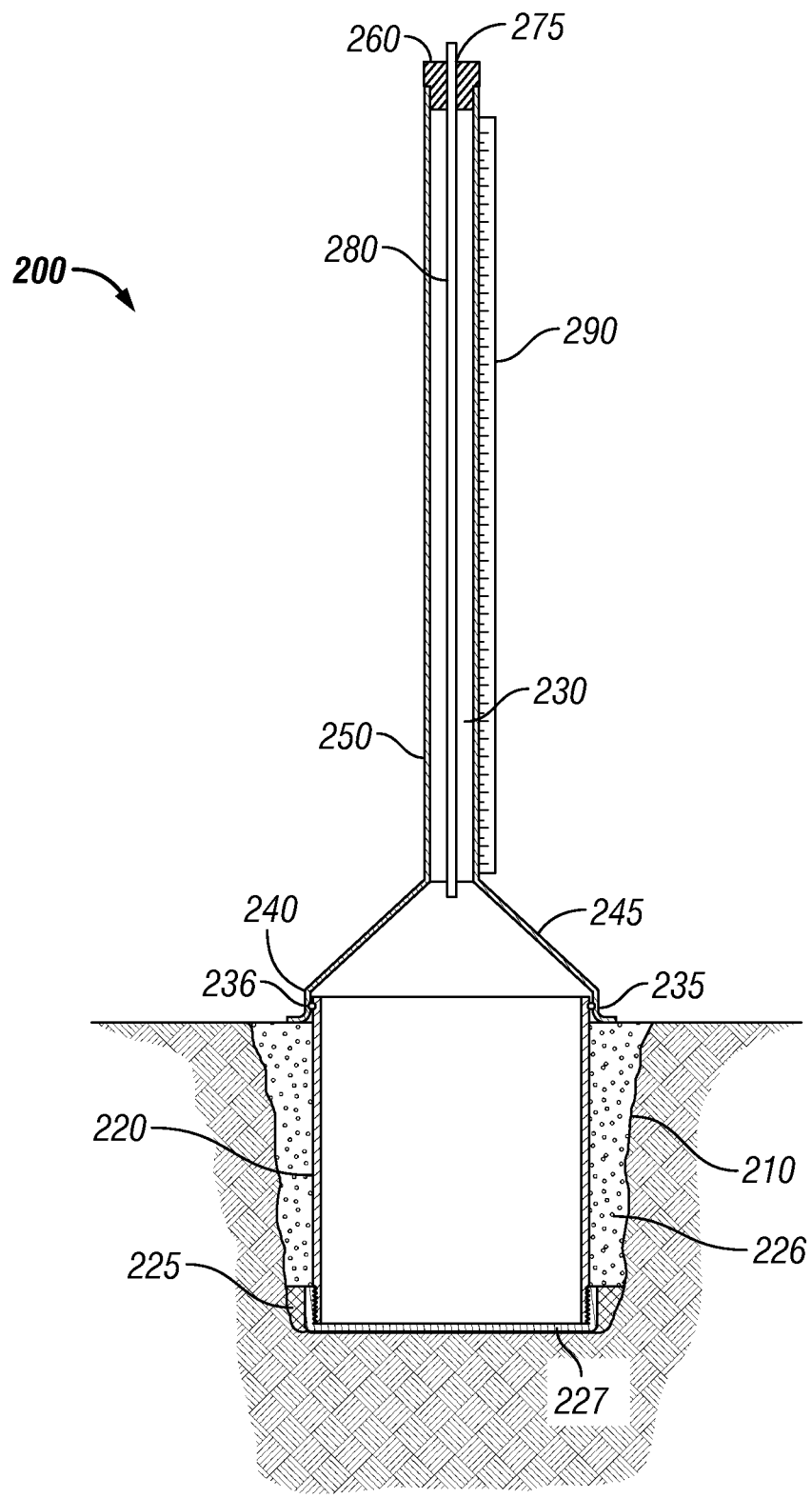
FIG. 2 is a sectioned side view of a permeameter probe for measuring hydraulic conductivity according to one embodiment of the present disclosure.

FIG. 2 illustrates one embodiment of a permeameter probe 200 in accordance with the present disclosure, which measures the hydraulic conductivity of soil using a constant head measurement. In the illustrated embodiment, the probe 200 is used in connection with a borehole 210. A casing 220 is placed in the borehole 210, wherein an annular sealant 225 is placed around the bottom of the casing 220. A secondary sealant 226 may also be located between the outer walls of the casing 220 and the walls of the borehole 210. In some embodiments, the permeameter probe 200 may also comprise a sock 227 located at the bottom of the casing.

The permeameter probe 200 further comprises a standpipe 230, located directly on top of the casing 220. According to the illustrated embodiment, the standpipe 230 is of unitary construction and is formed from a substantially transparent material. The standpipe 230 comprises a base section 240 and a top section 250, with a transitional section 245 between the base section 240 and the top section 250, the transitional section 245 having a substantially conical shape. The base section 240 comprises a lower lip 235, which engages the outer surface of the casing 220. In some embodiments, the base section 240 may further comprise an o-ring 236, which aids in forming a seal between the lower lip 235 and the casing 220. At the top of the top section 250 is a stopper 260, such as of rubber. The stopper 260 provides a seal at the top of the top section. A mariotte tube 280 is situated within the standpipe 230. In the illustrated embodiment, the mariotte tube 280 passes through the seal at the top of the standpipe, exiting the standpipe 230 through a hole 275 in the rubber stopper 260. The permeameter probe 200 further comprises a readable scale 290, attached to and running along the outside of the top section 250 of the standpipe 230. Alternatively, the readable scale 290 may be provided as a series of marks (e.g., etched or printed) on the top section 250, wherein the top section 250 essentially becomes a graduated cylinder. The marks may also continue onto the transitional section 245.

Figure 3:
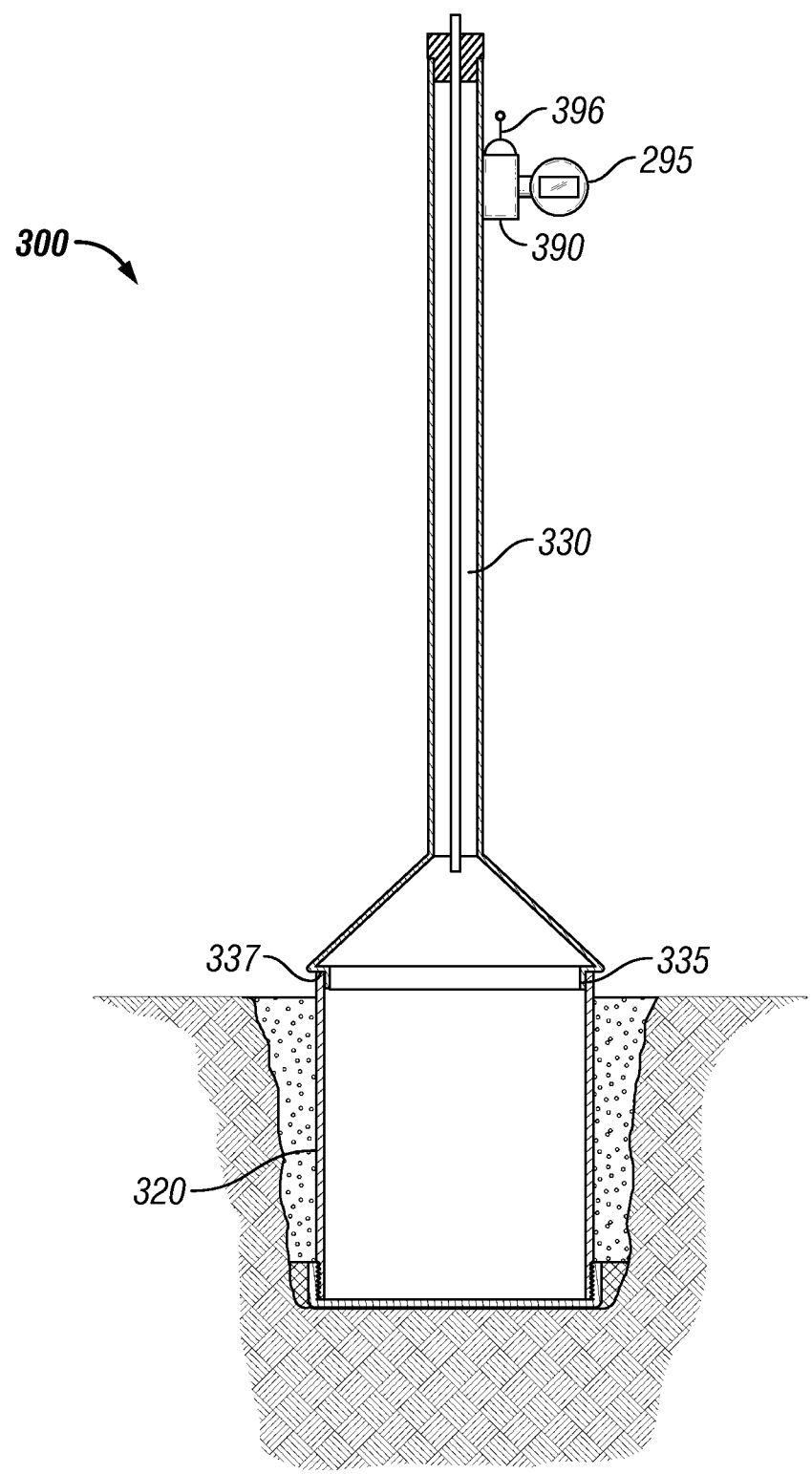
FIG. 3 is a sectioned side view of a permeameter probe for measuring hydraulic conductivity according to another embodiment of the present disclosure.

FIG. 3 illustrates an alternative embodiment of a permeameter probe 300, wherein the standpipe 330 comprises a lower lip 335 that engages the inner surface of the casing 320. In the embodiment illustrated in FIG. 3, the lower portion of the standpipe 330 further comprises an edge 337, which rests upon the top of the casing 320. The illustrated embodiment further comprises an electronic measurement device 390, which is connected to a digital display 395 and a transmitter 396.

Figures 4, 5:
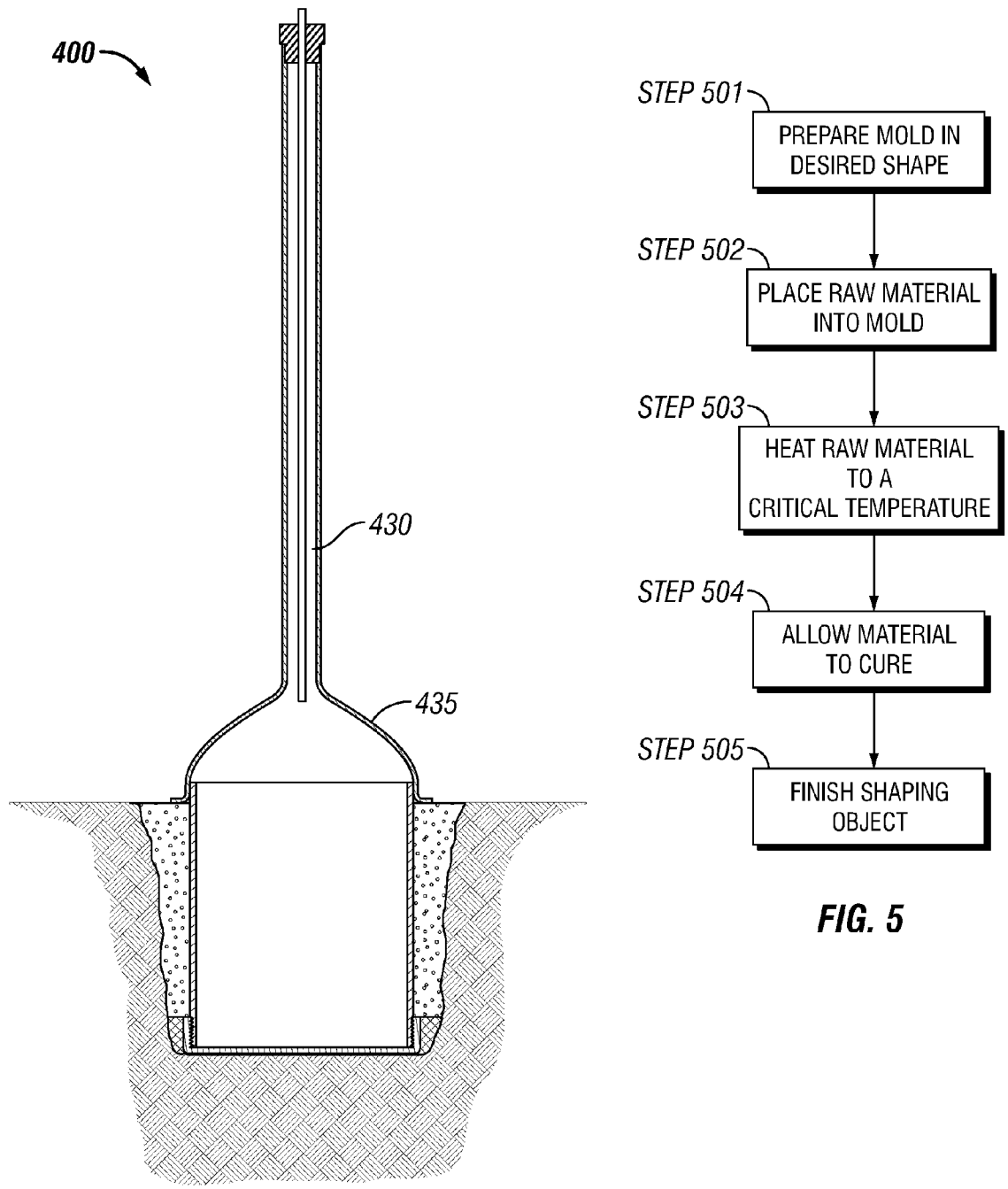
FIG. 4 is a sectioned side view of a permeameter probe for measuring hydraulic conductivity according to another embodiment of the present disclosure.
FIG. 5 is a flowchart outlining a method for manufacturing a standpipe for a permeameter probe in accordance with one aspect of the present disclosure.

FIG. 4 illustrates another alternative embodiment of a permeameter probe 400, wherein the standpipe 430 comprises a transitional section 435 with a substantially curvilinear shape.

Referring again to FIG. 2, the depth and diameter of the borehole 210, and the corresponding features of the casing 220, may be determined in accordance with the intended application; e.g., the intended use of the land, the soil conditions, etc. The borehole 210 and casing 220 are typically circular in cross-section, the borehole 210 being typically formed, (at least initially), using an auger, or the like. In many examples, the borehole is then finished by hand, such as by using hand tools. The outer diameter of the casing 220 is necessarily smaller than the smallest diameter of the borehole 210, at least down to the desired depth. A borehole extension of appropriate depth may also be used if desired, as may be apparent to one with skill in the art.

In various embodiments, both the annular sealant 225 and the secondary sealant 226 may be prepared using materials that are compatible with ambient geologic and geohydraulic conditions, as may be apparent to one having ordinary skill in the art. Bentonite is one example of a material that is commonly used.

The standpipe 230 of the illustrated embodiments comprises a base section 240, a transitional section 245, and a top section 250. Each of the sections has a circular cross-section, in a horizontal plane, and may be formed about a single axis. The diameter of the base section 240 is substantially larger than the diameter of the top section 250; approximately at least a ratio of 3:1, wherein the base section 240 is approximately 6-18 inches in diameter and the top section 250 is approximately 1-4 inches in diameter. By specifying a top section diameter that is substantially smaller than the diameter of the base section 240, the hydraulic conductivity test can be accomplished in a shorter time. Potential changes in the temperature of the water placed in the top section should also be considered, however, as a smaller diameter may cause the water therein to increase in temperature, which may affect the results of the test. In the illustrated embodiment, the diameter of the base section 240 is approximately 12 inches and the diameter of the top section 250 is approximately 2.125 inches.

When constructed for a constant-head hydraulic conductivity test, the permeameter probe 200 of the present disclosure is assembled with rubber stopper 260 placed in the top end of the top section 250. The rubber stopper 260 creates a seal with the inner surface of the top section 250 to enable the test to be conducted with a constant head pressure. Because air bubbles may be present in the system, or may percolate from the soil at the bottom of the borehole 210 as it is displaced by the water, the standpipe 230 may also be provided with a mariotte tube 280. The mariotte tube 280 exits the top end of the top section through a hole 275 in rubber stopper 260. The hole 275 may be slightly smaller than the outer diameter of the mariotte tube 280 in order to maintain the seal created by rubber stopper 260.

The standpipe 230 is advantageously constructed as a single, unitary structure. As shown in FIGS. 2-4, a transitional section 245 is included therein connecting the base section 240 to the top section 250. By providing a constantly decreasing diameter in a vertical direction along the axis of the standpipe 230, the transitional section 245 provides many advantages over the prior art. For example, the functionality of the lower lip and the unitary construction of the standpipe allow the system to be assembled without the need for couplings. As a result, the standpipe is much less likely to incur failures or leaks over time in comparison to the prior art.

The embodiments shown in FIGS. 2 and 3 illustrate a transitional section 245 that is substantially conical in shape. Alternatively, the transitional section may take another form, such as the substantially curvilinear shaped transitional section 445 of FIG. 4.

As shown in FIG. 2, the contact between the lower lip 235 and the outer surface of the casing 220 forms a pressure fitting sufficient to prevent water from leaking out of the permeameter probe 200, and also prevents air from entering into the standpipe 230 when in operation. The effectiveness of this fitting may be aided by the inclusion of an o-ring 236.

In the embodiment illustrated in FIG. 3, the standpipe 330 has a lower lip 335 formed to create a pressure fitting against an inside wall of the casing 320, wherein an outside diameter of the lower lip 335 is slightly larger than the inside diameter of the casing. In this instance, the outside diameter of the base section 340 may be formed to be larger than that of the lower lip 335, thereby creating an edge 337, which enables the standpipe 330 to rest on the top of the casing 320.

The permeameter probe 200 of the present disclosure may also be constructed with a scale that aids the user in determining the level of the water at a given time. In FIG. 2, the scale 290 is shown as being attached to the exterior of the standpipe 230, but may be in the form of etched, engraved, or printed marks on the standpipe 230, wherein the standpipe 230 essentially forms a graduated cylinder. Alternatively, as shown in the embodiment illustrated in FIG. 3, the hydraulic conductivity test may be performed by using an electronic measurement device 390, which may employ magnetic, sonic, or other electronic measurement schemes to determine the level of a liquid in the standpipe 330 at a given time. The electronic measurement device may further comprise a digital display 395, which allows the user to take an accurate reading of the electronic measurement device 390. Alternatively, the electronic measurement device may also be equipped with a transmitter 396 for sending measurement data to a remote location.

FIG. 5 illustrates one embodiment of an exemplary method for constructing a standpipe for use in a permeameter probe. In the illustrated embodiment, a mold is prepared in the desired shape of a standpipe, the standpipe having a top section, base section, and a transitional section (step 501). The mold of the present disclosure includes any type of suitable mold, mandrel, or the like. The mold approximating the chosen shape of the standpipe. In various embodiments, the mold may be prepared in the form of a standpipe as discussed in connection with the various embodiments above, wherein the standpipe comprises a bottom section, a transitional section, and a top section. Alternatively, the mold may be prepared in the shape of the bottom and transitional sections of the standpipe, wherein the top section of the standpipe is provided in the form of a clear pipe of a desired diameter and length and the step of finishing the shape of the object comprises adhering or welding the clear pipe to the top of the transitional section formed in the mold.

The desired raw material is then placed in the mold (step 502). The raw material may, for example, be a resin for forming an acrylic or PVC structure, or the like. The raw material may also be provided as molten glass or some other liquid which hardens into a unitary structure when cooled. In the examples above, the material is chosen for its ability to maintain a good seal with the casing and may also be chosen for transparency.

The raw material is then heated to a critical temperature, (e.g., melting temperature), to allow a transformation into a unitary piece (step 503). Alternatively, the step of heating the material may occur prior to placing the material in the mold, wherein the step of placing the raw material into the mold comprises pouring the molten raw material into the mold. The proper order of operations may be determined according to the chosen material in accordance with known methods.

After the material has cured (step 504) the object is finished into the final shape of the standpipe (step 505). In some embodiments, the step of finishing the shape of the object (step 505) may comprise removing burrs or defects after the material has cured. Also, as discussed above, the step may also comprise welding or adhering the top section of the standpipe (or a portion thereof) to the top of the structure. Further, this step may also comprise having an optional scale engraved, etched, or otherwise placed on an outer surface of the top section.

As will be appreciated by those of skill in the art, the rate of water level change in the standpipe will vary depending on the permeability of the soil at the permeameter site. Where the permeability is relatively low, the low rate of water level change in the standpipe can significantly lengthen the time required for the test, since it can be difficult to accurately read very small water level changes with the standpipe configuration shown in FIGS. 2-4. For example, when beginning testing at a given site, it may not initially be known whether the borehole hydraulic conductivity at that site will be $1\times10^{-5}$ or $1\times10^{-9}$ cm/s until after that site is initially tested in the field. Sometimes after testing is first begun, it will be found that the water level inside the standpipe barely changes over the course of many hours. In such a situation, it can take a very long time (e.g. a few weeks) to complete the test properly at that site.

Advantageously, an alternative standpipe design has been developed that can allow accurate reading of relatively small volume changes in a reasonable time frame. Shown in FIG. 6A is a cross-sectional side view of an embodiment of a three tube permeameter probe 600 for measuring hydraulic conductivity according to the present disclosure. A detail view of the top of the standpipe 650 is provided in FIG. 7. Like the other embodiments discussed above, the permeameter probe 600 is configured to be used in connection with a borehole in which a casing 620 is placed in the manner discussed above.

Like the embodiments discussed above, the permeameter probe 600 includes a substantially transparent standpipe 630 of unitary construction having a base section 640 and a top section 650, with a conical transitional section 645 there between. The base section 640 includes a lower lip 635, which engages the outer surface of the casing 620, and can also include an o-ring 636, forming a base seal between the lower lip 635 and the casing 620. The permeameter probe 600 can also include a readable scale (not shown) running along the outside of the top section 650 of the standpipe 630, or a series of etched or printed marks, or some other measuring device as discussed above.

Advantageously, this permeameter probe 600 includes an interchangeable multi-tube design. Like the embodiments described above, at the top of the top section 650 is a rubber stopper 660a that provides a seal at the top of the standpipe. A secondary standpipe 652a exits the standpipe 630 through a hole 675a in the rubber stopper 660a. The secondary standpipe 652a extends from above the top of the top section 650, down into the conical transitional section 645, and includes a top rubber stopper 662a at its top end and a bottom rubber stopper 662b at the bottom end, to provide a water tight seal. A mariotte tube 680 is situated within the secondary standpipe 652a, and exits the standpipe 630 through a pair of holes 677a, 677b in the top and bottom rubber stoppers 662a, 662b, respectively.

By virtue of the top and bottom rubber stoppers 662a, 662b, the secondary standpipe 652a is sealed at both ends (aside from passage of the mariotte tube 680) and contains only air. Because of this configuration, water 685 in the top section 650 of the standpipe will occupy only the annular space between the inner wall of the top section 650 and the outer wall of the secondary standpipe 652a. This configuration essentially amounts to changing the volume of water per unit height of the standpipe 650 by changing the cross sectional area in the standpipe. To decrease the volume of water in the standpipe the mariotte tube 680 is placed inside the secondary standpipe 652a and sealed off with rubber stoppers 662 to create an air space. This secondary standpipe 652a is then placed inside the standpipe and sealed off at the top with the stopper 660 to create the constant-head device. In this way, a portion of the volume of the standpipe that would otherwise be taken up by water is now taken up by air. Consequently, the volume of water per unit of height of the top section 650 is less than if the entire top section were full (other than the diameter of the mariotte tube), as in the other embodiments discussed above, causing the rate of change of the water level to increase for a given permeability rate.

Advantageously, the diameter of the secondary standpipe 652 can vary, and can be selected for various conditions. For example, the configuration of FIG. 6B includes a secondary standpipe 652b that is of a larger diameter than the secondary standpipe of 652a of FIG. 6A, so that annular space for the water in the top section 650 of the standpipe is smaller than that of FIG. 6A. To accommodate this larger diameter secondary standpipe 652b, the rubber stopper 660b of FIG. 6B has a larger hole 675b. Rubber stoppers 660 can be configured having holes 675 of various diameters, so that a secondary standpipe of a desired size and the appropriate rubber stopper 660 can be selected for any given situation. With this configuration, the volume of water in the top section 650 can be modified and better matched with the rate of infiltration. This allows for flexibility using one device for a range of hydraulic conductivities.

Figure 6:
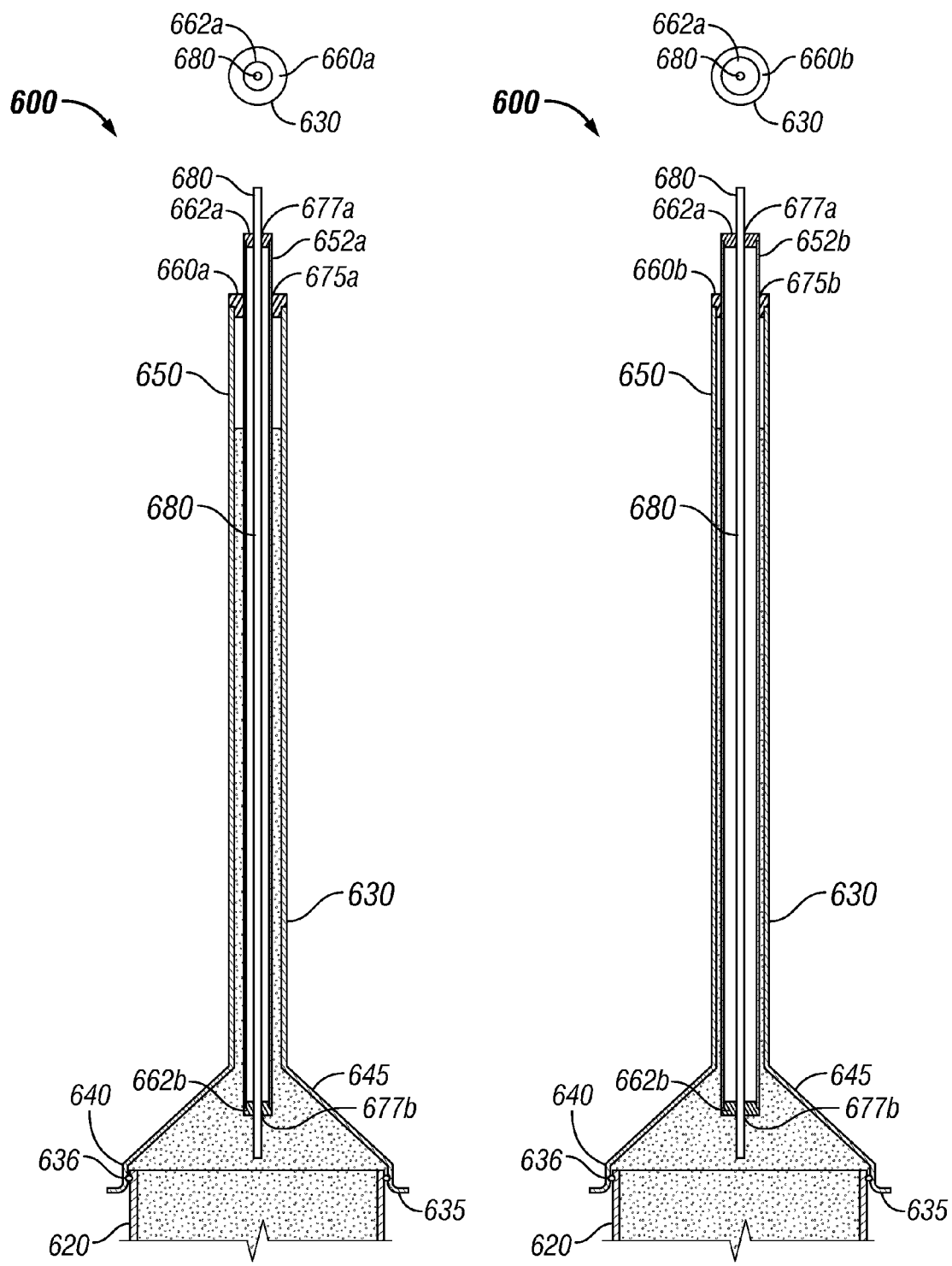
FIGS. 6A and 6B are sectioned side views of two embodiments of permeameter probes having different sizes of mariotte tubes for measuring hydraulic conductivity according to another embodiment of the present disclosure.
Figure 7:
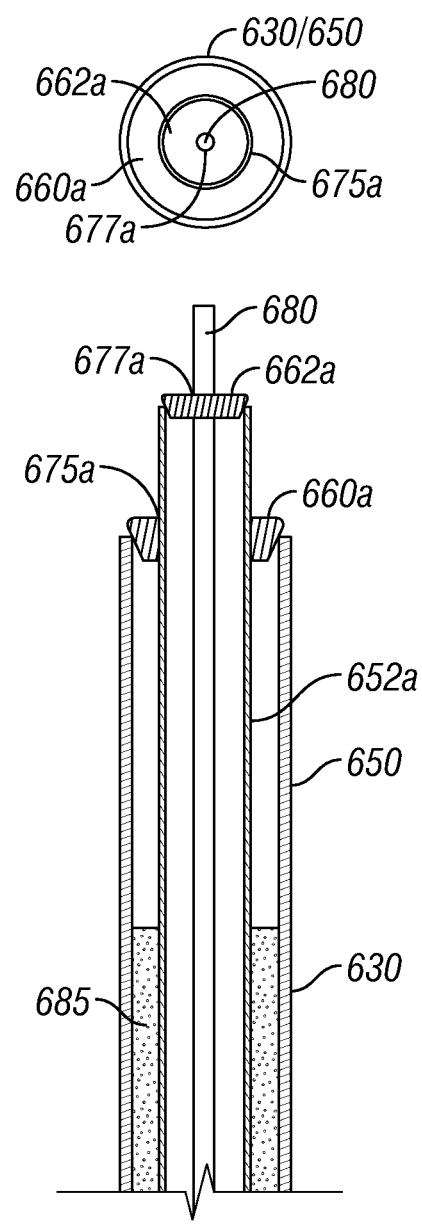
FIG. 7 is a detail view of the top of the permeameter probe and mariotte tube of one of the embodiments of FIG. 6.

To get accurate permeability readings, a smaller volume of water per unit height of the standpipe (i.e. a larger secondary standpipe) is desirable for a lower flow rate, whereas a larger volume of water per unit height of the standpipe (i.e. a smaller secondary standpipe) is desirable for a higher flow rate. The configuration shown in FIGS. 6 and 7 provides flexibility by decreasing or increasing the volume of water in the standpipe without needing a new permeameter top. This allows better matching of the secondary standpipe with the hydraulic conductivity at a given site.

It is recognized that the diameter of the secondary standpipe 652 can have an effect on the accuracy of the system in view of temperature changes. As the diameter of the secondary standpipe 652 increases, the volume of water in the top section 650 decreases, and this can increase the error potential caused from thermal effects. One step that has been found to help reduce potential thermal error effects from this source is to insulate the borehole to reduce the amount of thermal expansion both of the water and the components of the permeameter probe.

It should be emphasized that the above-described embodiments of the present apparatus and process are merely possible examples of implementations and merely set forth for a clear understanding of the principles of the disclosure. Many different embodiments of the disclosure described herein may be designed and/or fabricated without departing from the spirit and scope of the disclosure. All these and other such modifications and variations are intended to be included herein within the scope of this disclosure and protected by the following claims. Therefore the scope of the disclosure is not intended to be limited except as indicated in the appended claims.

What is claimed is:

1. An apparatus for measuring hydraulic conductivity using borehole infiltration, comprising:
    a standpipe, including
        a base section, having a circular cross-section with a first diameter;
        a top section, having a top end and a circular cross-section with a second diameter, the second diameter being substantially smaller than the first diameter; and
        a transitional section, between the base section and the top section, the transitional section having a diameter that changes gradually along a vertical axis,
    wherein the standpipe is formed of a single, integral piece of a substantially transparent material;
    a top seal located at the top end of the top section of the standpipe; and
    a mariotte tube located within the standpipe, the mariotte tube having a lower end located near the base section and an upper end located above the top end of the top section, wherein the mariotte tube extends through the top seal.

2. The apparatus of claim 1, wherein the top seal comprises a stopper, and the mariotte tube passes through a hole in the stopper that is slightly smaller than an outer diameter of the mariotte tube, forming an air tight seal.

3. The apparatus of claim 1, further comprising a secondary standpipe, located within the standpipe, having a lower end located below the top section and having a lower seal, and an upper end located above the top end and having an upper seal, the upper end of the secondary standpipe extending through the top seal of the standpipe, the mariotte tube being located within the secondary standpipe and extending through the upper seal and the lower seal.

4. The apparatus of claim 1, wherein the first diameter falls within the range of about 12 to about 18 inches, and the second diameter is less than about 4 inches.

5. The apparatus of claim 1, wherein the standpipe is formed of a single piece of substantially transparent acrylic material.

6. The apparatus of claim 1, wherein the transitional section is substantially cone-shaped.

7. An apparatus for measuring hydraulic conductivity of soil in a borehole formed in the soil at a location to be tested, comprising:
    a casing, having a circular cross-section with a first diameter, the casing having a bottom that rests upon a bottom of the borehole;
    an annular casing seal disposed around the bottom of the casing;
    a standpipe, of unitary construction, having a base section with a lower lip that forms a substantially waterproof standpipe seal with the casing,
    wherein the standpipe is formed of a single piece of substantially transparent acrylic material.

8. The apparatus of claim 7, wherein the standpipe seal between the base section and the casing comprises a pressure fitting.

9. The apparatus of claim 7, further comprising a secondary casing seal, disposed between a wall of the borehole and an outside surface of the casing.

10. The apparatus of claim 7, wherein the lower lip is in contact with an inner wall of the casing, thereby forming the standpipe seal, the base section comprising an edge which rests upon a top of the casing.

11. The apparatus of claim 7, further comprising an electronic measurement device.

12. The apparatus of claim 11, wherein the electronic measurement device includes a transmitter.

13. The apparatus of claim 7, wherein the standpipe further comprises:
    a top section, having a circular cross-section with a second diameter substantially smaller than the first diameter;
    a transitional section, between the base section and the top section, having a diameter that changes gradually along a vertical axis;
    a top seal, located in the top end of the top section; and
    a mariotte tube, located within the standpipe, the mariotte tube having a lower end located near the base section and an upper end located above the top end of the top section, wherein the mariotte tube extends through the top seal.

14. The apparatus of claim 13, wherein the lower lip is in contact with an inner wall of the casing, thereby forming the substantially waterproof standpipe seal, the base section comprising an edge which rests upon a top of the casing.

15. The apparatus of claim 13, further comprising a secondary standpipe, located within the standpipe, having a lower end located below the top section and having a lower seal, and an upper end located above the top end and having an upper seal, the upper end of the secondary standpipe extending through the top seal of the standpipe, the mariotte tube being located within the secondary standpipe and extending through the upper seal and the lower seal.

* * * * *